United States Patent [19]

Shikata et al.

[11] Patent Number: 5,037,837
[45] Date of Patent: Aug. 6, 1991

[54] PHENOXYPROPYLAMINE DERIVATIVES OR SALTS THEREOF AND ANTIULCER AGENTS CONTAINING THE SAME

[75] Inventors: Yoshiyuki Shikata; Ryoichi Nanba; Isamu Endo; Masashi Isozaki; Tadashi Okumura; Masazumi Miyakoshi; Shingo Koyama, all of Kanagawa, Japan

[73] Assignee: Terumo Kabushiki Kaisha, Tokyo, Japan

[21] Appl. No.: 607,670

[22] Filed: Nov. 1, 1990

[30] Foreign Application Priority Data

Nov. 2, 1989 [JP] Japan ................. 1-284910

[51] Int. Cl.$^5$ ............ A61K 31/445; A61K 31/40; C07D 211/06; C07D 207/04
[52] U.S. Cl. ............................ 514/331; 514/408; 514/617; 546/234; 548/578; 564/170
[58] Field of Search ............ 564/170; 546/234; 548/578; 514/331, 408, 617

[56] References Cited

U.S. PATENT DOCUMENTS 4,293,557 10/1981 Shibata et al. ............ 514/331
4,482,566 11/1984 Hirai et al. ............ 548/578
4,564,623 1/1986 Hirai et al. ............ 514/408
4,847,269 7/1989 Clark et al. ............ 514/331

OTHER PUBLICATIONS

C.A. 95, 24523k, "Substituted Phenoxypropylamide Derivatives", 1981.
C.A. 95, 42701w, "Aminoalkylbenzene Derivatives and their Pharmaceutical Compositions", 1981.
C.A. 95, 80465e, "Phenoxypropylamine Derivatives, Pharmaceutical Compositions etc.", 1981.

Primary Examiner—Richard L. Raymond
Assistant Examiner—Susan P. Treanor
Attorney, Agent, or Firm—Burns, Doane, Swecker & Mathis

[57] ABSTRACT

Novel phenoxypropylamine derivative having the formula (I)

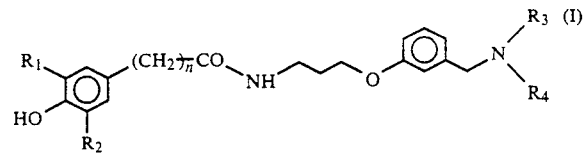

wherein $R_1$ and $R_2$ represent a hydrogen atom, a hydroxy group, a lower alkyl group or a lower alkoxy group, and $R_3$ and $R_4$ represent a lower alkyl group, or $R_3$ and $R_4$ taken together represent a group having the formula $(CH_2)_m$ wherein m represents 4 or 5, and n represents an integer of from 2 to 6 or a pharmaceutically acceptable salt thereof.

The compounds are useful as a 5-lipoxygenase inhibitor and an antiulcer agent.

3 Claims, No Drawings

PHENOXYPROPYLAMINE DERIVATIVES OR SALTS THEREOF AND ANTIULCER AGENTS CONTAINING THE SAME

BACKGROUND OF THE INVENTION

1. Field of the Invention

This invention relates to novel phenoxypropylamine derivatives and pharmaceutically acceptable salts thereof.

The invention also relates to 5-lipoxygenase inhibitors and antiulcer agents containing the above compounds.

2. Description of the Prior Art

Development of histamine $H_2$ antagonists has facilitated treatment of ulcers but posed a current big problem of recurrence after a stop of the drug administration. Because the recurrence is believed to be due to reduction of the protective factor it is desired to develop drugs concurrently having an inhibitory activity against gastric acid secretion and an activity of reinforcing the protective factor. In addition, since leucotrienes are suspected to participate in healing process of chronic ulcers, inhibition of the biosynthesis of leucotrienes is possibly effective in the therapy of ulcers.

DETAILED DESCRIPTION OF THE INVENTION

As a result of syntheses of various phenoxypropylamine derivatives and extensive studies on their physiological actions, we have found that the phenoxypropylamine derivatives of the invention have a potent inhibitory activity on secretion of gastric acid and protective factor-reinforcing activity as well as an inhibitory activity on the action of 5-lipoxygenase. This invention has been completed on the basis of the above findings. The phenoxypropylamine derivatives of the invention are useful for the therapy of ulcers.

It is therefore an object of the invention to provide phenoxypropylamine derivatives and pharmaceutically acceptable salts thereof. Another object of the invention is to provide 5-lipoxygenase inhibitors and antiulcer agent containing the same.

Thus, this invention is directed to phenoxypropylamine derivatives having the formula (I)

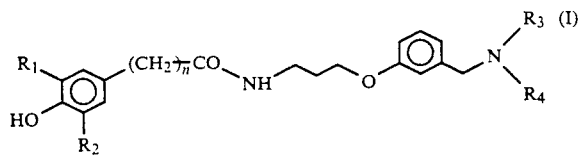

wherein $R_1$ and $R_2$ represent a hydrogen atom, a hydroxy group, a lower alkyl group or a lower alkoxy group, and $R_3$ and $R_4$ represent a lower alkyl group, or $R_3$ and $R_4$ taken together represent a group having the formula $-CH_2)_m$ wherein m represents 4 or 5, and n represents an integer of from 2 to 6 or salts thereof.

Examples of the salts include a salt with an inorganic acid such as the hydrochloride and the sulfate and a salt with an organic acid such as the acetate and the tartrate.

In the definition of the above-mentioned substituents, the lower alkyl group means a straight- or branched-chain alkyl group having 1-4 carbon atoms, such as methyl, ethyl, n-propyl, iso-propyl, n-butyl, iso-butyl and tert-butyl. The lower alkoxy group means an alkoxy group with the alkyl moiety being an alkyl group as defined above such as methoxy, ethoxy, n-propoxy, iso-propoxy, n-butoxy, iso-butoxy and tert-butoxy.

The phenylpropylamine derivatives (I) of the invention are produced by condensing a carboxylic acid derivative having the formula (II)

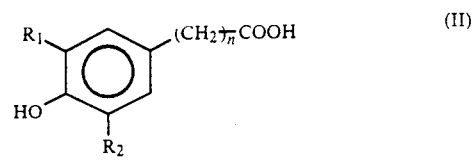

wherein $R_1$, $R_2$ and n have the same meanings as set forth above and an amine derivative having the formula (III)

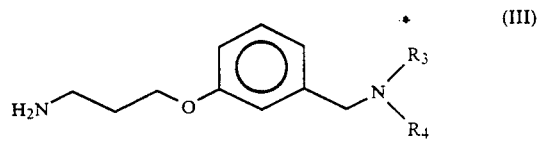

wherein $R_3$ and $R_4$ have the same meanings as set forth above followed by a deprotection reaction. It is desirable to use in the condensation reaction a condensing agent such as N,N'-dicyclohexylcarbodiimide (DCC). The carboxylic acid derivative (II) is preferably reacted with thiazolidinethione or the like reagent in the presence of a catalyst such as dimethylaminopyridine to form an active carboxylic acid derivative before the reaction with the amine derivative (III). The reaction is conveniently carried out by contacting the reactants (II) and (III) in the presence of a solvent such as dichloromethane, carbon tetrachloride, benzene, toluene, ether or tetrahydrofuran and the abovementioned condensing agent at 0° C. to room temperature for 30 min. to 24 hours.

After the completion of the reaction the solvent is removed by distillation, and an oily residue is extracted with an appropriate solvent and purified by such means as chromatography to obtain the desired product.

The phenoxypropylamine derivatives of the invention is used as a 5-lipoxygenase inhibitor or an antiulcer agent. The dosage is generally 10-2000 mg, preferably 20-600 mg per day for a human adult though variable depending upon conditions of the patient. Preferably, it is divided into one to three doses per day as needed by conditions of the patient. Route of administration may be in any form suitable for the administration. Oral administration is especially desirable, intravenous administration being also feasible.

The compounds of the invention can be administered either alone or in admixture, as one of the active ingredients, with pharmaceutical carriers or excipients and other additives by a conventional method, in various forms such as tablets, sugar-coated tablets, powders, capsules, granules, suspension, emulsion and injectables. Examples of the carrier or excipient are calcium carbonate, calcium phosphate, starch, glucose, lactose, dextrin, alginic acid, mannitol, talc and magnesium stearate.

Examples and test examples are given below to describe the invention in more detail, but the invention is to be in no way limited thereto.

EXAMPLE 1

To a solution of 1.67 g of 5-(4-methoxymethoxy-3-methoxyphenyl)pentanoic acid and 0.89 mg of 2-mercaptothiazoline in 70 ml of dichloromethane were added at room temperature 1.54 g of dicyclohexylcarbodiimide and 6.07 g of 4-dimethylaminopyridine. The mixture was stirred for 40 min. followed by filtration with suction. The filtrate was washed with a 1N NaOH solution and saturated aqueous sodium chloride and dried over magnesium sulfate. The solvent was removed by distillation under reduced pressure, and the residue subjected to chromatography on silica gel. From the fraction eluted with dichloromethane was obtained 1.49 g of N-[5-(4-methoxymethoxy-3-methoxyphenyl)pentanoyl]-thiazolidine-2-thione.

A solution of 0.71 g of N-[5-(4-methoxymethoxy-3methoxyphenyl)pentanoyl]-thiazoline-2-thione and 0.70 g of 3-[3-(1-piperidinylmethyl)phenoxy]propylamine in 20 ml of dichloromethane was stirred at room temperature for 16 hours followed by filtration with suction. The filtrate was washed with a 1N aqueous sodium hydroxide and saturated aqueous sodium chloride and dried over magnesium sulfate. The solvent was then removed by distillation under reduced pressure to afford 1.18 g of N-[3-(3-(1-piperidinylmethyl)phenoxy)-propyl]-5-(4-methoxymethoxy-3-methoxyphenyl)-pentylamide.

To a solution of 1.18 g of N-[3-(3-(1piperidinylmethyl)phenoxy)propyl]-5-(4-methoxymethoxy-3methoxyphenyl)pentylamide in 15 ml of methanol and 5 ml of water was added 0.54 g of p-toluenesulfonic acid. The mixture was then stirred at 50° C. for 17 hours, and the solvent removed by distillation under reduced pressure. To the residue was added water, and the mixture extracted with dichloromethane. The dichloromethane solution was washed with saturated aqueous sodium chloride and dried over magnesium sulfate. The solvent was removed by distillation under reduced pressure, and the residue subjected to chromatography on silica gel. From the fraction eluted with 10% methanol-dichloromethane was obtained 0.89 g of N-[3-(3(1-piperidinylmethyl)phenoxy)propyl]-5-(4-hydroxy-3methoxyphenyl)pentylamide. Spectroscopic data of the product support structure of the formula (IV) below.

NMR (CDCl$_3$) δ: 3.34(2H,8,J=6 Hz), 3.40(2H,s), 3.75(3H,s), 4.00(2H,t,J=6 Hz), 6.00(1H,m).

thiazoline were dissolved in 60 ml of dichloromethane followed by the addition of 2.91 g of dicyclocarbodiimide and 0.17 g of 4-dimethylaminopyridine. The mixture was stirred for 16 hours. The reaction mixture was filtered, and the filtrate washed with 1N aqueous sodium hydroxide and water and dried over anhydrous sodium sulfate. The solvent was then removed by distillation under reduced pressure, and the residue subjected to column chromatography on silica gel. From the fraction eluted with methylene chloride was obtained 4.10 g of N-[5-(4-methoxymethoxyphenyl)pentanoyl)-2-thiazolidine-2-thione.

To a solution of 1.16 g of 3-[3-(1-piperidinylmethyl)-phenoxy]propylamine in 20 ml of dichloromethane was added 1.59 g of N-[5-(4-methoxymethoxyphenyl)pentanoyl]-2-thiazolidine-2-thione. The mixture was stirred at room temperature for 2 hours. The reaction mixture was washed with a 1N aqueous sodium hydroxide, water and saturated aqueous sodium chloride and dried over anhydrous sodium sulfate. The solvent was then removed by distillation under reduced pressure, and the residue subjected to column chromatography on silica gel. From the fraction eluted with 1% methanol-chloroform was obtained 0.98 g of N-[3-(3-(1piperidinylmethyl)phenoxy)propyl]-5-(4-methoxymethoxyphenyl)pentylamide.

To a solution of 0.98 g of N-[3-(3-(1piperidinylmethyl)phenoxy)propyl]-5-(4-methoxymethoxyphenyl)-pentylamide in 20 ml of methanol was added 2 ml of 6N-hydrochloric acid, and the mixture stirred at 50° C. for 20 min. The solvent was removed by distillation under reduced pressure followed by the addition of a saturated aqueous sodium hydrogen carbonate. The mixture was extracted with chloroform, and the organic layer washed with saturated aqueous sodium chloride and dried over anhydrous magnesium sulfate. The solvent was removed by distillation under reduced pressure, and the residue subjected to column chromatography on silica gel. From the fraction eluted with 2% methanol-chloroform was obtained 0.62 g of N-[3-(3-(1piperidinylmethyl)phenoxy)propyl]-5-(4-hydroxyphenyl)-pentylamide. Spectroscopic data of the product support structure of the formula (V) below.

NMR (CDCl$_3$) δ: 3.40(2H,s), 6.00(1H,m).

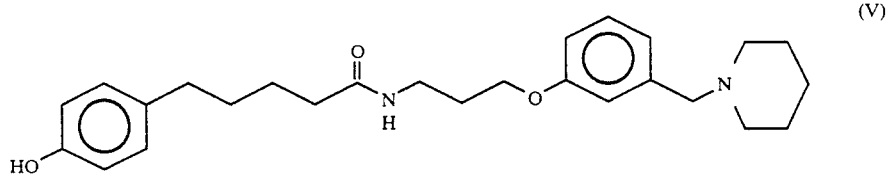

(V)

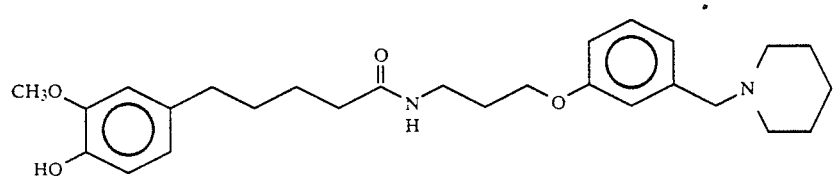

(IV)

EXAMPLE 2

In an atmosphere of argon 3.36 g of 5-(4-methoxymethoxyphenyl)pentanoic acid and 1.68 g of 2-mercapto-

EXAMPLE 3

In the atmosphere of argon 5-(3,5-di-tert-butyl-4-hydroxy)phenylpentanoic acid (0.23 g), 2-mercaptothiazoline (0.12 g) and 4-dimethylaminopyridine (0.01 g) were dissolved in methylene chloride (5 ml). To the solution cooled to 0° C. was added N,N'-dicyclohexylcarbodiimide (0.19 g). Then, the mixture was stirred at room temperature for 2.5 hours. The reaction mixture was filtered, and the filtered matters washed with benzene. The filtrate was concentrated under reduced pressure, and the residue subjected to column chromatography on silica gel. From the fraction eluted with n-hexane-ethyl acetate (2:1 v/v) was obtained 0.30 g of N-[5-(3,5-di-tert-butyl-4-hydroxyphenyl)pentanoyl]-thiazolidine-2-thione.

Next, to a solution of 3-[3-(1-piperidinylmethyl)-phenoxy]propylamine (0.26 g) in methylene chloride (4 ml) was added a solution of N-[5-(3,5-di-tert-butyl-4-hydroxyphenyl)pentanoyl]-thiazolidine-2-thione (0.30 g) in methylene chloride (6 ml) followed by stirring at room temperature for 80 min. To a reaction solution was added a 1N aqueous potassium hydroxide, and the mixture extracted twice with chloroform. The organic layer was dried over anhydrous magnesium sulfate, filtered and concentrated under reduced pressure, and the residue subjected to column chromatography on silica gel. From the fraction eluted with chloroform-methanol (50:1 v/v) was obtained 0.31 g of N-[3-(3-(1-piperidinylmethyl)phenoxy)propyl]-5-(3,5-di-tert-butyl-4-hydroxyphenyl)pentylamide. Spectroscopic data of the product support structure of the formula (VI) below.

NMR (CDCl₃) δ: 1.41(18H,s), 3.39(2H,s), 3.99(2H,t,J=6 Hz), 6.17(1H,m).

g of 3-(3-(1-piperidinyl)phenoxypropylamine in 50 ml of dichloromethane was stirred at room temperature for 16 hours. The reaction mixture was filtered with suction, and the filtrate washed with a 1N aqueous sodium hydroxide and then with saturated aqueous sodium chloride and dried over magnesium sulfate. The solvent was removed by distillation, and the residue subjected to column chromatography on silica gel. From the fraction eluted with chloroform-methanol (25:1) was obtained 1.15 g of N-[3-(3-(1-piperidinylmethyl)phenoxy)propyl]-5-(4-methoxymethoxy-3,5dimethoxyphenyl)-pentylamide.

A solution of 1.15 g of N-[3-(3-(1-piperidinylmethyl)phenoxy)propyl]-5-(4-methoxymethoxy-3,5dimethoxyphenyl)pentylamide in 20 ml of methanol was mixed with a solution of 498 mg of paratoluenesulfonic acid monohydrate in 5 ml of water followed by heating to 50° C. and stirring for 5 hours. After cooling the reaction mixture was diluted with water and then extracted with ethyl acetate. The ethyl acetate layer was washed with a saturated aqueous sodium hydrogen carbonate and then with saturated aqueous sodium chloride and dried over magnesium sulfate. The solvent was removed by distillation, and the residue subjected to column chromatography on silica gel. From the fraction eluted with chloroform-methanol (20:1) was obtained 0.44 g of N-[3-(3-(1-piperidinylmethyl)phenoxy)-propyl]-5-(4-hydroxy-3,5-dimethoxyphenyl)pentylamide. Spectroscopic data of the product support structure of the formula (VII) below.

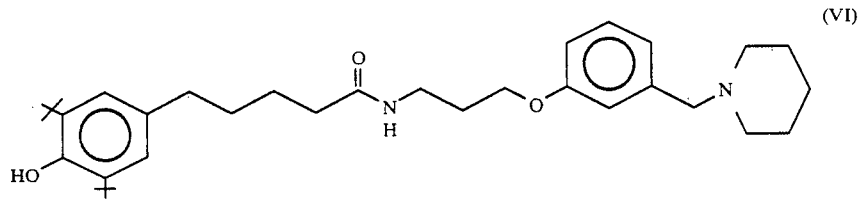

EXAMPLE 4

NMR (CDCl₃) δ: 3.41(2H,br,s), 3.72(6H,s), 4.00(2H,t,J=6 Hz), 6.33(2H,s), 6.00(1H,br,s).

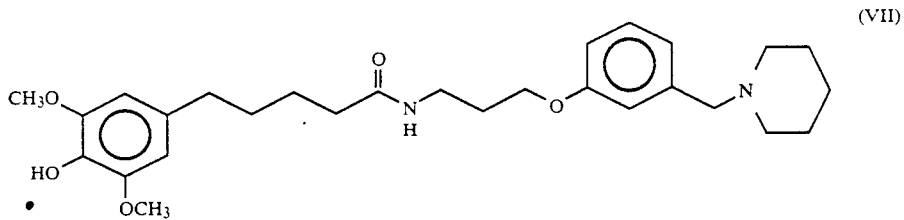

To a solution of 0.88 g of 5-(4-methoxymethoxy-3,5-dimethoxyphenyl)pentanoic acid and 0.42 g of 2-mercaptothiazoline in 30 ml of dichloromethane were added 0.73 g of dicyclohexylcarbodiimide and 36 mg of 4-dimethylaminopyridine at room temperature followed by stirring for 16 hours. The reaction mixture was filtered with suction, and the filtrate washed with a 1N aqueous NaOH solution and then with saturated aqueous sodium chloride and dried over sodium sulfate. The solvent was removed by distillation, and the residue subjected to column chromatography on silica gel. From the fraction eluted with dichloromethane was obtained 1.15 g of N-[5-(4-methoxymethoxy-3,5-dimethoxyphenyl)pentanoyl)-thiazolidine-2-thione.

A solution of 1.15 g of N-[5-(4-methoxymethoxy-3,5-dimethoxyphenyl)pentanoyl]-thiazolidin-2-one and 0.87

EXAMPLE 5

In an atmosphere of argon 4.03 g of 3-(4-methoxymethoxy-3-methoxyphenyl)propionic acid and 1.79 g of 2-mercaptothiazoline were dissolved in 80 ml of dichloromethane followed by the addition of 3.10 g of dicyclohexylcarbodiimide and 0.21 g of 4-dimethylaminopyridine. The mixture was stirred at room temperature for 15 hours, and the reaction mixture was filtered. The filtrate was washed with a 1N aqueous sodium hydroxide, water and saturated aqueous sodium chloride and dried over anhydrous magnesium sulfate. The solvent was removed by distillation under reduced pressure, and the residue subjected to column chromatography on silica gel. From the fraction eluted with methylene chloride was obtained 5.07 g of N-[3-(4-methoxymethoxy-3-methoxyphenyl)propanoyl]-thiazolidine-2thione.

To a solution of 2.18 g of 3-[3-(1-piperidinylmethyl)-phenoxy]propylamine in 40 ml of dichloromethane was added 3.00 g of N-[3-(4-methoxymethoxy-3-methoxyphenyl)propanoyl]-thiazolidine-2-thione followed by stirring at room temperature for 4 hours. The reaction mixture was washed with a 1N aqueous sodium hydroxide, water and saturated aqueous sodium chloride and dried over anhydrous magnesium sulfate. Then, the solvent was removed by distillation under reduced pressure, and the residue subjected to column chromatography on silica gel. From the fraction eluted with chloroform was obtained 2.54 g of N-[3-(3-(1-piperidinylmethyl)phenoxy)propyl]-3-(4-methoxymethoxy-3-methoxyphenyl)propylamide.

To a solution of 2.54 g of N-[3-(3-(1-piperidinylmethyl)phenoxy)propyl]-3-(4-methoxymethoxy-3methoxyphenyl)propylamide in 20 ml of methanol was added 5 ml of 6N-hydrochloric acid followed by stirring at 50° C. for 1 hour. The solvent was removed by distillation under reduced pressure. To the residue was added a saturated aqueous sodium hydrogen carbonate followed by extraction with dichloromethane. The organic layer was washed with water and saturated aqueous sodium chloride and dried over anhydrous magnesium sulfate. Then, the solvent was removed by distillation under reduced pressure, and the residue subjected to column chromatography on silica gel. From the fraction eluted with 2% chloroform-methanol was obtained 1.68 g of N-[3-(3-(1-piperidinylmethyl)phenoxy)propyl]-3-(4-hydroxy-3-methoxyphenyl)propylamide. Spectroscopic data of the product support structure of the formula (VIII) below.

NMR (CDCl₃) δ: 3.40(2H,s), 3.80(3H,s), 5.96(1H,m).

EXAMPLE 6

To a solution of 130 mg of ethyl chlorocarbonate in 5 ml of dichloromethane were dropwise added a solution of 180 mg of 4-(4-hydroxy-3-methoxyphenyl)butanoic acid and 120 mg of triethylamine in 5 ml of dichloromethane. To the mixture previously stirred at −60° C. for 1 hour was added a solution of 150 mg of 3-(1-piperidinylmethyl)phenoxy)propylamine in 5 ml of dichloromethane, and the resulting mixture was stirred at from −60° C. to room temperature for 19 hours and diluted with dichloromethane. The dichloromethane solution was washed with water and saturated aqueous sodium chloride and dried over anhydrous magnesium sulfate. Removal of the solvent by distillation under reduced pressure afforded 510 mg of N-[3-(3-(1-piperidinylmethyl)phenoxy)propyl]-4-(4-ethoxycarbonyloxy-3-methoxyphenyl)butylamide.

To a solution of 510 mg of N-[3-(3-(1-piperidinylmethyl)phenoxy)propyl]-4-(4-ethoxycarbonyloxy-3methoxyphenyl)butylamide in 5 ml of methanol and 3 ml of water was added 30 mg of sodium hydroxide followed by stirring at 50° C. for 1 hour. Then, the solvent was removed by distillation under reduced pressure. Water was added to the residue and the mixture was extracted with dichloromethane. The organic layer was washed with saturated aqueous sodium chloride and dried over anhydrous magnesium sulfate. Then the solvent was removed by distillation under reduced pressure and the residue subjected to column chromatography on silica gel. From the fraction eluted with 5% methanol-dichloromethane was obtained 120 mg of N-[3-(3-(1-piperidinylmethyl)phenoxy)propyl]-4-(4-hydroxy-3-methoxyphenyl)butylamide.

The spectroscopic data of the product support structure of the formula (IX) below.

NMR (CDCl₃) δ: 3.40(2H,s), 3.78(3H,s), 3.93(2H,t,J=6 Hz), 6.00(1H,m).

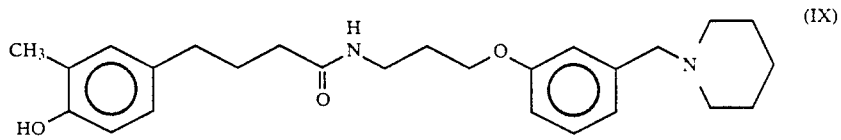

(IX)

EXAMPLE 7

In an atmosphere of argon 5.04 g of 5-(3,4-dimethoxymethoxyphenyl)pentanoic acid and 2.02 g of 2-mercaptothiazoline were dissolved in 100 ml of dichloromethane followed by the addition of 3.49 g of dicyclohexylcarbodiimide and 0.21 g of 4-dimethylaminopyridine. The mixture was stirred at room temperature for 18 hours, and the reaction mixture filtered. The filtrate was washed with a 1N aqueous sodium hydroxide and water and dried over anhydrous sodium sulfate. Then, the solvent was removed by distillation under reduced pressure, and the residue subjected to column chromatography on silica gel. From the fraction eluted with

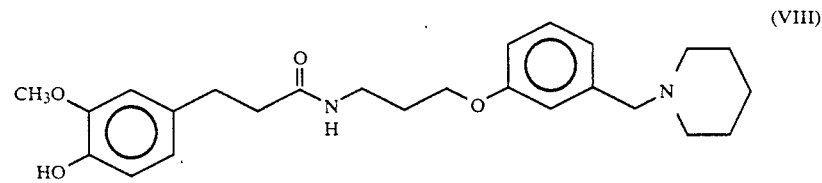

(VIII)

methylene chloride was obtained 5.26 g of N-[5-(3,4-dimethoxymethoxyphenyl)pentanoyl]-2-thiazolidine-2-thione.

To a solution of 3.27 g of 3-[3-(1-piperidinylmethyl)-phenoxy]propylamine in 30 ml of chloroform was added 5.26 g of N-[5-(3,4-dimethoxymethoxyphenyl)-pentanoyl]-2-thiazolidine-2-thione followed by stirring at room temperature for 3 hours. The reaction mixture was washed with a 1N aqueous sodium hydroxide and saturated aqueous sodium chloride and dried over anhydrous sodium sulfate. Then, the solvent was removed by distillation under reduced pressure, and the residue subjected to column chromatography on silica gel. From the fraction eluted with 2% methanol-chloroform was obtained 6.24 g of N-[3-(3-(1-piperidinylmethyl)-phenoxy)propyl]-5-(3,4-dimethoxymethoxyphenyl)pentylamide.

To a solution of 2.00 g of N-[3-(3-(1-piperidinylmethyl)phenoxy)propyl]-5-(3,4-dimethoxymethoxyphenyl)pentylamide in 40 ml of methanol was added 4 ml of 6N-hydrochloric acid followed by stirring at 50° C. for 30 min. The solvent was removed by distillation under reduced pressure. To the residue was added a saturated aqueous sodium hydrogen carbonate followed by extraction with chloroform. The organic layer was washed with saturated aqueous sodium chloride and dried over anhydrous sodium sulfate. Then, the solvent was removed by distillation under reduced pressure, and the residue subjected to column chromatography on silica gel. From the fraction eluted with 4% methanol-chloroform was obtained 1.02 g of N-[3-(3-(1piperidinylmethyl)phenoxy)propyl]-5-(3,4dihydroxyphenyl)pentylamide. Spectroscopic data of the product support structure of the formula (X) below.

NMR (CDCl$_3$) δ: 3.36(2H,s), 6.02(1H,m).

tives of the invention not shown in the table also have a high 5-lipoxygenase-inhibiting activity.

50% inhibitory concentration as referred to in the table means concentration of a phenol derivative required for controlling the production of 5-lipoxygenase as described above to 50% by introducing said phenol derivative when production of 5-HETE without phenol derivative of the invention is taken as 100%.

(2) Inhibitory activity against ethanol hydrochloric acid ulcer

To SD male rats (weighing 150–250 g) fasted for 24 hours was administered orally a phenol derivative of the invention at a dose of 30 mg/kg bodyweight. One hour later, a hydrochloric acid solution in ethanol (containing 150 mM hydrochloric acid in 60% ethanol) was orally given in a volume of 0.5 ml/100 g bodyweight.

One hour later, the animals were sacrificed with ether. The stomach was excised and, after formalin treatment, measured for the length (mm) of lesions developed in glandular portions of the stomach. Total

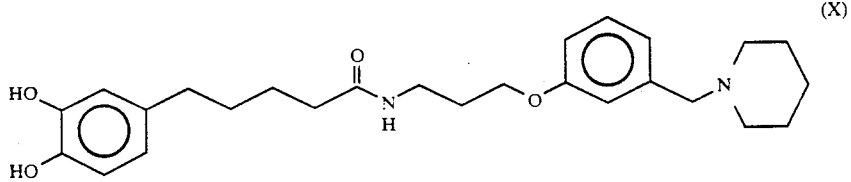

(X)

Test example (1) 5-Lipoxygenase-inhibiting activity

A suspension of rat-origin basophilic leukemia cell strain RBL-1 in an Eagle basal medium (manufactured by Gibco Laboratories) containing 10% FCS is cultivated in a 5% CO$_2$ incubator at 37° C. The culture is then centrifuged at 4° C. to collect cells. The cells are re-suspended in a phosphate buffer solution at pH 7.4 to a cell density of $1.0 \times 10^7 – 3.0 \times 10^7$ cells/ml. The suspended cells are treated by an ultrasonic cell blender and then centrifuged at 15,000 rpm at 4° C. for 30 min. The supernatant is employed as an enzyme solution of a 5-lipoxygenase. In test tubes are placed 50 μg of arachidonic acid and a phenol derivative of the invention to be tested. To each of the test tubes are added 0.30 ml of phosphate buffer, 0.20 ml of the enzyme solution as prepared above and 5 μl of a 100 mM CaCl$_2$ (calcium chloride) solution. The mixture is allowed to react at 37° C. for 15 min. To the reaction mixture, after ice-cooling, is added one drop of 1N HCl (hydrochloric acid), and the resulting mass is extracted with 2 ml of ethyl acetate. The extract is concentrated to dryness followed by the addition of 100 μl of methanol for use as a test specimen.

Said specimen is injected into octadecylsilane (ODS) reverse phase high performance liquid chromatography (HPLC), eluted with methanol - acetonitrile - water - acetic acid (15:45:35:0.01). Peak for 5-HETE (5-(s)-hydroxy-6,8,11,14-eicosatetraenoic acid), a 5-lipoxygenase product detected in approximately 25 min. is measured. The 5-lipoxygenase-inhibiting activity is determined by decrease in the peak for said 5-lipoxygenase product. As a result of the test remarkable 5-lipoxygenase-inhibiting activities were found as shown in the table below. It was demonstrated that phenol derivalength of the lesions per animal was taken as ulcer index.

As shown in the table, marked antiulcer activities were found by the test. It was demonstrated that phenol derivatives of the invention not shown in the table also have a similar antiulcer activity.

Percent inhibition of ulceration as referred to in the table is a value obtained by reducing from 1 the ulcer index for the rat with a phenol derivative of the invention orally given divided by the ulcer index for the orally nonadministered rat and multiplying the value by 100. The calculation is conducted by the formula shown below.

Percent inhibition of ulceration (%) =

$$\left(1 - \frac{\text{Ulcer index for thiazole derivative orally administered rat}}{\text{Ulcer index for thiazole derivative orally non-administered rat}}\right) \times 100$$

(3) Antagonistic action against histamine H$_2$ receptors

Excised right atrium of Hartley male guinea pigs (weighing 450–550 g) was used. Thus, the guinea pig was fainted by strongly hitting the occipital region, and then the chest opened to isolate the heart. The isolated heart was immersed in a Krebs-Henseleit nutrient solution at 30° C. which had sufficiently been aerated with 95% O$_2$+5% CO$_2$. The right atrium with the right cardiac auricle attached thereto was separated carefully enough to avoid damages. Blood vessels and tissues attached around the separated organ were removed. Both ends of the separated right cardiac auricle were held with threaded Serfin, and the thread at one end was fixed in a tissue tank filled with the nutrient solution, and the thread at the other end connected to a tension measuring and recording instrument and loaded with 1-g weight. The nutrient solution in the tissue tank was maintained at a temperature of 30° C. and consistently aerated with a 95% $O_2$+5% $CO_2$ gas. The nutrient solution was exchanged every 5–10 min.

After spontaneous contractions of the isolated right atrium specimen were stabilized, and the heart rate became constant, histamine was cumulatively introduced into the tissue tank. Thus, histamine was introduced cumulatively starting at $10^{-7}$M and gradually at $3\times10^{-7}$M, $10^{-6}$M, $3\times1^{-6}$M, and so on. When the heart rate became constant at a given concentration, the concentration was further increased, and the cumulative introduction of histamine was continued until the heart rate no more increased. There was then determined a histamine dose-response curve.

Antagonistic action of the phenol derivatives of the invention against histamine $H_2$ receptors was tested using the isolated right atrium specimen previously employed for determining a histamine dose-response curve. Thus, said specimen with the increased heart rate by the cumulative introduction of histamine was repeatedly washed with a nutrient solution to remove the histamine. When the heart rate was decreased by the histamine removal to a constant level, a phenol derivative of the invention was introduced into the tissue tank. After the introduction of said phenol derivative, histamine was cumulatively introduced sufficiently to determine a histamine dose-response curve in the presence of said phenol derivative. Antagonistic action of the phenol derivatives of the invention is determined by measuring the distance (mm) at 50% reaction between the dose-response curve in the absence of said phenol derivative and one in the presence of said phenol derivative and calculating $pA_2$ on the basis of the distance from the Van Rossum simplified table.

Results of the test indicated remarkable antagonistic actions against histamine $H_2$ receptors as shown in the table. It was confirmed that the phenol derivatives of the invention not shown in the table also have an antagonistic action against histamine $H_2$ receptors.

Note that the $pA_2$ in the table means a -log value of the concentration of a phenol derivative of the invention necessary for parallel displacement of the histamine dose-response curve to the side of a twice increase in concentration.

TABLE

Pharmacological profile of the phenol derivatives.

| Structural formula | Example No. | 5-Lipoxygenase inhibiting activity 50% Inhibition conc. (M) | Inhibitory activity against ethanol hydrochloric acid ulcer Percent inhibition of ulceration (%) | Antagonistic action against histamine $H_2$ receptors $pA_2$ |
|---|---|---|---|---|
| (3-methoxy-4-hydroxyphenyl)-alkyl amide with piperidinomethyl phenoxy group | 1 | $6.1 \times 10^{-6}$ | 89.5 | 7.24 |
| (4-hydroxyphenyl)-alkyl amide with piperidinomethyl phenoxy group | 2 | $1.2 \times 10^{-4}$ | 33.4 | 6.50 |
| (3-X-4-hydroxyphenyl)-alkyl amide with piperidinomethyl phenoxy group | 3 | $2.0 \times 10^{-5}$ | 42.9 | 5.59 |
| (3-methoxy-4-hydroxy-5-methoxyphenyl)-alkyl amide with piperidinomethyl phenoxy group | 4 | $1.3 \times 10^{-5}$ | 62.5 | 6.31 |
| (3-methoxy-4-hydroxyphenyl)-alkyl amide with piperidinomethyl phenoxy group | 5 | $3.2 \times 10^{-5}$ | 48.0 | 6.20 |

TABLE-continued
Pharmacological profile of the phenol derivatives

| Structural formula | Example No. | 5-Lipoxygenase inhibiting activity 50% Inhibition conc. (M) | Inhibitory activity against ethanol hydrochloric acid ulcer Percent inhibition of ulceration (%) | Antagonistic action against histamine $H_2$ receptors $pA_2$ |
|---|---|---|---|---|
| (CH₃O, HO-phenyl)-CH₂CH₂-C(O)-NH-CH₂CH₂CH₂-O-(phenyl)-CH₂-N(piperidine) | 6 | $8.9 \times 10^{-6}$ | 76.5 | 7.30 |
| (HO, HO-phenyl)-CH₂CH₂CH₂-C(O)-NH-CH₂CH₂CH₂-O-(phenyl)-CH₂-N(piperidine) | 7 | $5.9 \times 10^{-6}$ | 83.7 | 6.85 |

Acute toxicity

An acute toxicity test by oral administration was run using ICR male mice (5 week-old). The $LD_{50}$ value was more than 200 mg/kg or more higher with any of the compounds of the invention thereby confirming higher safety than the effective dose.

According to the present invention there are provided novel phenoxypropyl derivatives or salts thereof and 5-lipoxygenase inhibitors and antiulcer agents containing the same.

The compounds of the invention have been found to have a 5-lipoxygenase-inhibiting activity and an antiulcer activity. Thus, said compounds can inhibit the action of 5-lipoxygenase thereby inhibiting production of leukotrienes such as LTC4 and LTD4 which are formed by the action of 5-lipoxygenase. Accordingly, said derivatives can promote healing of chronic ulcers.

As the compounds of the invention can inhibit ulceration, they are also useful as a therapeutic agent for gastric and other ulcers.

What is claimed is:

1. A phenoxypropylamine derivative having the formula (I)

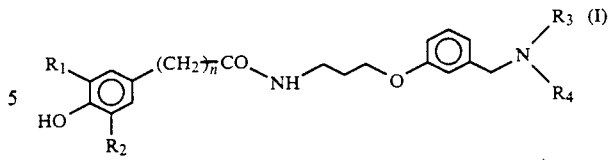

wherein $R_1$ and $R_2$ represent a hydrogen atom, a hydroxy group, a lower alkyl group or a lower alkoxy group, and $R_3$ and $R_4$ represent a lower alkyl group, or $R_3$ and $R_4$ taken together represent a group having the formula $-(CH_2)_m$ wherein m represents 4 or 5, and n represents an integer of from 2 to 6 or a pharmaceutically acceptable salt thereof.

2. A phenoxypropylamine derivative according to claim 1 wherein $R_1$ represents a hydrogen atom, a lower alkyl group, a lower alkoxy group, $R_2$ represents a hydrogen atom, a lower alkyl group, a lower alkoxy group, n is an integer of from 2 to 4 and $R_3$ and $R_4$ taken together represent a group having the formula $-(CH_2)_m$ wherein m represents 5.

3. A pharmaceutical composition containing a therapeutically effective amount of the phenoxypropylamine derivative according to claim 1 and a pharmaceutical carrier.

* * * * *